US00PP30922P2

(12) United States Plant Patent
Egger

(10) Patent No.: US PP30,922 P2
(45) Date of Patent: Oct. 1, 2019

(54) ***HEUCHERA* PLANT NAMED 'TNHEUGB'**

(50) Latin Name: ***Heuchera* hybrid**
Varietal Denomination: TNHEUGB

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,137

(22) Filed: Oct. 1, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by purple black to black leaf color, large leaves with slightly ruffled and rounded lobes, very light pink flowers on upright flowering stems, performing well in sun or shade, a large, tall mounding habit with an excellent crown count, and excellent vigor.

1 Drawing Sheet

Botanical denomination: *Heuchera* hybrid.
Variety designation: 'TNHEUGB'.
Trademark designation: Grande™ Black.

BACKGROUND OF THE INVENTION

The present invention relates to a new and distinct cultivar of *Heuchera* and given the cultivar name of 'TNHEUGB'. *Heuchera* is in the family Saxifragaceae. *Heuchera* 'TNHEUGB' originated as a controlled cross using *Heuchera* 'B107-3', a proprietary, unpatented, unnamed seedling as the seed parent, and *Heuchera* 'Macks Silver', a proprietary, unpatented, unreleased seedling as the pollen parent. These parents are a result of breeding using *Heuchera villosa* with proprietary hybrid lines. *Heuchera* 'TNHEUGB' was bred to be a landscape plant with a large habit and large leaves for sun or shade. The trademark designations is 'Grande™ Black.'

Compared to the seed parent, *Heuchera 'B*107-3', the new cultivar has larger, black leaves rather than silver leaves and a larger habit.

Compared to the pollen parent, *Heuchera* 'Macks Silver', the new cultivar has black leaves rather than silver leaves, a larger habit, and more crowns.

Compared to *Heuchera* 'TNHEUNEB', U.S. Plant Pat. No. 30,583, the new cultivar has a taller habit and black to purple leaves that are larger, more lobed, and wavier.

Compared to *Heuchera* 'Mocha', U.S. Plant Pat. No. PP18,386, the new cultivar has more glabrous leaves that are purple black to black rather than brown.

This new *Heuchera* is uniquely distinguished by:

1. purple black to black leaf color,
2. large leaves with slightly ruffled and rounded lobes,
3. very light pink flowers on upright flowering stems,
4. performing well in sun or shade,
5. a large, tall mounding habit with an excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2015 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a one-year-old plant of *Heuchera* 'TNHEUGB' growing in the show garden in June in Canby, Oreg.

DETAILED PLANT DESCRIPTION

The following is a detailed description of the new *Heuchera* cultivar based on observations taken in late October of nine-month-old specimens growing in the trial field in full sun in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Form.*—Basal rosette, herbaceous perennial.

*Hardiness.*—USDA Zone 4 to 9.

*Size.*—Grows to 30 cm tall from top of foliage to ground, 58 cm wide.

*Number of crowns.*—About 16.
*Habit.*—Large, mounding.
*Vigor.*—Excellent.

Leaf:
*Type.*—Simple.
*Arrangement.*—Rosette.
*Shape.*—Broadly ovate.
*Number.*—About 160.
*Blade size.*—Grows to 16 cm long and 15.5 cm wide.
*Venation.*—Palmate.
*Lobing/Division.*—4 to 6 palmate lobes.
*Margins.*—Broadly crenate.
*Apex.*—Mucronulate.
*Base.*—Cordate, overlapping.
*Surface texture.*—Glandular-puberulent on both sides.
*Leaf rugosity.*—Slight.
*Petiole description.*—Grows to 18 cm long and 4.2 mm wide, glandular hairs; color closest to Greyed Purple N186C.
*Leaf color.*—Year round, new leaves, topside closest to Greyed Purple N186A tinted heavily with Green 137B, veins between Brown 200A and Greyed Purple N186A, bottom side closest to Purple N77B, veins closest to Purple N79B; older leaves, topside Greyed Purple N186A with veins between Brown 200A and Greyed Purple N186A, bottom side between Purple N77B and Purple N79C with veins closest to Purple N79C.

Inflorescence:
*Size.*—Grows to 6.5 cm wide and 15 cm long.
*Type.*—Upright thyrse.
*Number of flowers per thyrse.*—About 90.
*Flower density.*—Medium to light.
*Number of thyrse.*—3.
*Peduncle.*—Grows to 44 cm long and 3.5 mm wide at base with glandular hairs; Greyed Purple 187A.
*Pedicel.*—Grows to 2.5 mm long, with glandular hairs; Greyed Purple 187A.
*Bloom period.*—Late August to September in Canby, Oreg.

Flower bud:
*Size.*—3.5 mm wide and 5 mm long.
*Description.*—Glandular puberulent, ovoid, down facing.
*Color.*—Greyed Purple 186A on bottom half, blending to Yellow Green N144D on margins.

Flower:
*Type.*—Perfect.
*Shape.*—Campanulate.
*Attitude.*—Side and down facing.
*Size.*—6.2 mm long and 4 mm wide.
*Corolla description.*—5 petals, each 3 mm long and 1 mm wide, spatulate, margins entire, tip acute, glandular-puberulent on back side, glabrous inside, White NN155 on both sides.
*Calyx description.*—Campanulate, 4 mm long and 3 mm wide; 5 lobes each 2 mm wide and 2 mm long, oblong in shape, back side glandular-puberulent, glabrous inside, tip obtuse, margin entire, outside color Greyed Purple 186A on bottom half blending to Yellow Green N144D to tip.
*Stamen description.*—5 in number, filaments 1.5 mm long, White NN155, anthers 0.3 mm long, Greyed Orange 168A, pollen none, male sterile.
*Pistil description.*—1, 2-beaked, 4 mm long and 2 mm wide, ovary 2 mm long and 2 mm wide, Yellow 4C, style 2 mm long, Yellow 4C.
*Fragrance.*—None.
*Lastingness.*—Each thyrse blooms for about 3 weeks on the plant.

Seed: none seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

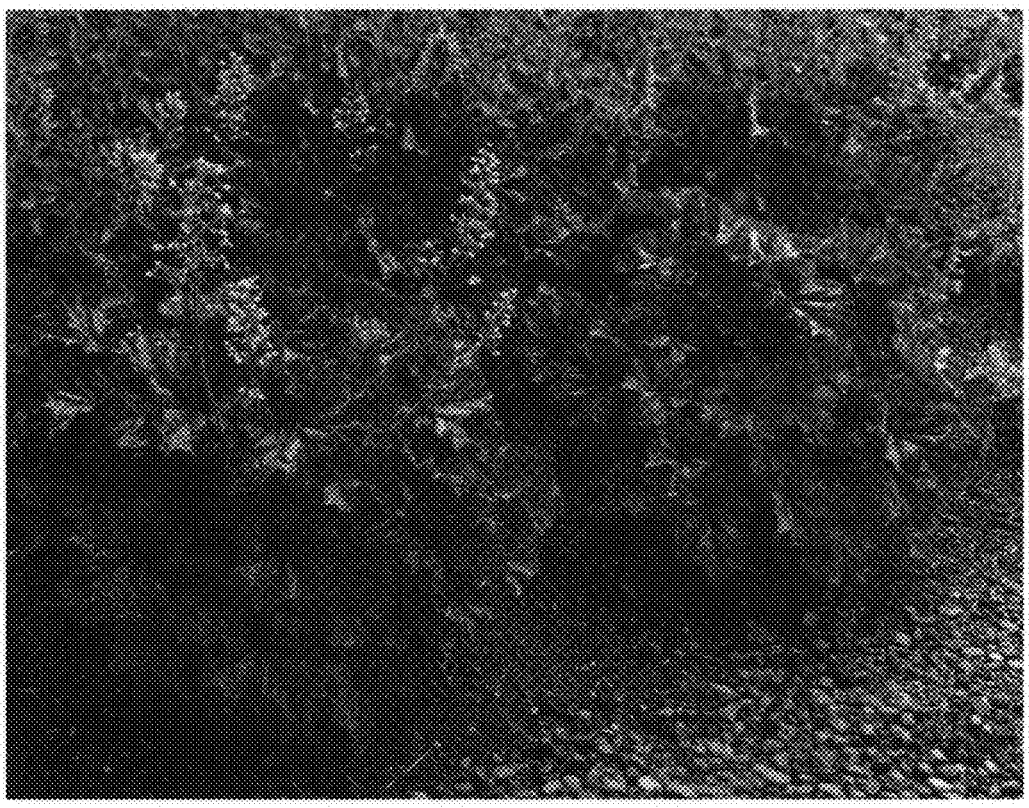

* * * * *